(12) United States Patent
Pastore et al.

(10) Patent No.: US 11,694,770 B2
(45) Date of Patent: Jul. 4, 2023

(54) VOLATILE ORGANIC COMPOUND DETECTION AND CLASSIFICATION

(71) Applicant: International Business Machines Corporation, Armonk, NY (US)

(72) Inventors: Vito Paolo Pastore, Lecce (IT); Simone Bianco, San Francisco, CA (US); Nimrod Megiddo, Palo Alto, CA (US); Andrea Fasoli, San Jose, CA (US); Aminat Adebiyi, San Jose, CA (US); Mohammed Abdi, San Jose, CA (US); Alberto Mannari, San Jose, CA (US); Luisa Dominica Bozano, Los Gatos, CA (US)

(73) Assignee: International Business Machines Corporation, Armonk, NY (US)

( * ) Notice: Subject to any disclaimer, the term of this patent is extended or adjusted under 35 U.S.C. 154(b) by 208 days.

(21) Appl. No.: 17/079,684

(22) Filed: Oct. 26, 2020

(65) Prior Publication Data

US 2022/0130491 A1    Apr. 28, 2022

(51) Int. Cl.
*G16C 20/20*    (2019.01)
*G16C 20/70*    (2019.01)
(Continued)

(52) U.S. Cl.
CPC .............. *G16C 20/20* (2019.02); *G16C 20/70* (2019.02); *G06N 3/00* (2013.01); *G06Q 50/00* (2013.01);
(Continued)

(58) Field of Classification Search
CPC ........ G16C 20/20; G16C 20/70; G16C 20/90; G16C 20/00; G06N 3/00; G06Q 50/00; H04L 67/00; Y02A 50/20
See application file for complete search history.

(56) References Cited

U.S. PATENT DOCUMENTS

| 7,424,619 B1* | 9/2008 | Fan | G06F 21/552 |
| | | | 713/188 |
| 2003/0037036 A1* | 2/2003 | Weare | G06F 16/683 |

(Continued)

FOREIGN PATENT DOCUMENTS

| CN | 102866179 A | 1/2013 |
| CN | 110084300 A | 8/2019 |
| CN | 110163247 A | 8/2019 |

OTHER PUBLICATIONS

Licen et al (Pattern Recognition and Anomaly Detection by Self-Organizing Maps in a Multi Month E-nose Survey at an Industrial Site. Sensors (Basel). Mar. 29, 2020;20(7):1887. doi: 10.3390/s20071887. PMID: 32235302; PMCID: PMC7180849) (Year: 2020).*

(Continued)

*Primary Examiner* — Daniel R Miller
*Assistant Examiner* — Christian T Bryant
(74) *Attorney, Agent, or Firm* — David K. Mattheis (57) ABSTRACT

Volatile organic compounds classification by receiving test data associated with detecting volatile organic compounds (VOCs), analyzing the test data according to a set of data features associated with known VOCs, determining a match between each feature of the test data and a corresponding feature of the set of data features, yielding a set of matches, defining a first degree of anomaly for the test data according to the set of matches, and classifying the test data according to the first degree of anomaly.

17 Claims, 5 Drawing Sheets

(51) Int. Cl.
*H04L 67/00* (2022.01)
*G16C 20/00* (2019.01)
*G06N 3/00* (2023.01)
*G06Q 50/00* (2012.01)
*G16C 20/90* (2019.01)

(52) U.S. Cl.
CPC ............. *G16C 20/00* (2019.02); *G16C 20/90* (2019.02); *H04L 67/00* (2013.01); *Y02A 50/20* (2018.01)

(56) References Cited

U.S. PATENT DOCUMENTS

| | | | | |
|---|---|---|---|---|
| 2013/0282550 A1* | 10/2013 | Sycoff | ................ | G06Q 30/0269 705/37 |
| 2015/0254555 A1* | 9/2015 | Williams, Jr. | ......... | G06N 3/084 706/14 |
| 2018/0180590 A1* | 6/2018 | Hall | ....................... | G16C 20/70 |
| 2019/0317079 A1* | 10/2019 | Trenholm | .............. | G16C 20/70 |
| 2020/0351283 A1* | 11/2020 | Salunke | .............. | H04L 63/1425 |
| 2021/0333270 A1* | 10/2021 | Mann | .................. | G01N 33/5058 |
| 2022/0067093 A1* | 3/2022 | Su | ........................ | G06F 16/9035 |

OTHER PUBLICATIONS

Combined Search and Examination Report dated Mar. 25, 2022 from GB Application No. GB2114081.9.
Loutfi et al., "Electronic noses for food quality: A review", Journal of Food Engineering 144 (2015) pp. 103-111, Available online Aug. 4, 2014, <http://dx.doi.org/10.1016/j.jfoodeng.2014.07.019>.
Mell et al., "The NIST Definition of Cloud Computing", Recommendations of the National Institute of Standards and Technology, Special Publication 800-145, Sep. 2011, 7 pages.
Zhang et al., "Abnormal Odor Detection in Electronic Nose via Self-Expression Inspired Extreme Learning Machine", IEEE Transactions on Systems, Man, and Cybernetics: Systems, vol. 49, No. 10, Oct. 2019, pp. 1922-1932.

* cited by examiner

VOLATILE ORGANIC COMPOUND DETECTION AND CLASSIFICATION

BACKGROUND

The disclosure relates generally to the detection and classification of volatile organic compounds. The disclosure relates particularly to detecting and classifying volatile organic compounds using a trained machine learning model.

Volatile organic compound (VOC) detection and classification has been, and still is, a challenging area for the research community. Sensors detect VOCs by integrating an array of partially specific, and uniquely selective, VOC-recognition sensors that are directly exposed to the target chemical analyte or the environment. The main components of the sensors are an array of gas sensors and a pattern-recognition algorithm, to learn the unique signatures of the VOCs to later accurately classify the unknown VOC in a supervised or unsupervised fashion.

SUMMARY

The following presents a summary to provide a basic understanding of one or more embodiments of the disclosure. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatuses and/or computer program products enable automatic classification of detected volatile organic compounds.

Aspects of the invention disclose methods, systems and computer readable media associated with volatile organic compound (VOC) classification by receiving test data associated with detecting volatile organic compounds, analyzing the test data according to a set of data features associated with known VOCs, determining a match between each feature of the test data and a corresponding feature of the set of data features, yielding a set of matches, defining a first degree of anomaly for the test data according to the set of matches, and classifying the test data according to the first degree of anomaly.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

In an embodiment, one or more components of the system can employ hardware and/or software to solve problems that are highly technical in nature (e.g., analyzing test data features according to a set of data features associated with known VOCs, determining a match between each feature of the test data and a corresponding feature of the set of data features, yielding a set of matches, defining a first degree of anomaly for the test data according to the set of matches, and classifying the test data according to the first degree of anomaly, etc.). These solutions are not abstract and cannot be performed as a set of mental acts by a human due to the processing capabilities needed to facilitate volatile organic compound classification, for example. Further, some of the processes performed may be performed by a specialized computer for carrying out defined tasks related to data classification. For example, a specialized computer can be employed to carry out tasks related to the classification of volatile organic compounds, or the like.

A volatile organic compound is transduced by an array of sensors resulting in a time-series voltage output from each sensor which is related to the VOCs with which each sensor gets in contact. The voltage output of each sensor may be analyzed in terms of transitions form a first voltage to a second voltage. Each voltage transition may be divided into equal temporal segments, such as five segments per transition. Each temporal segment of each transition may be characterized as a feature of that transition. In this manner, the set of voltage outputs from the sensor array during exposure to a VOC may be translated to a set of VOC related features. Similarly, the set of array sensor output voltages associated with exposure to a set of VOCs, such as the aroma bouquets associated with food or beverage items, may be translated to a set of features associated with the voltage transitions in the sensor outputs for the corresponding sets of VOCs. Disclosed embodiments enable the classification of new volatile organic compounds in terms of a set of previously classified volatile organic compounds utilized to train a machine-learning volatile organic compounds classification model.

The sensor-array output may be provided directly to an electronic-nose computing system executing disclosed embodiments, or the data may be recorded and provided to an external computing system executing disclosed embodiments.

In an embodiment, a method trains a machine-learning model using a set of labeled VOCs. Each VOC of the set may constitute a single VOC or a labeled set of VOCs such as the set of VOCs associated with a particular scent, or flavor. For each VOC, the method gathers electronic-nose voltage outputs.

In an embodiment, each sensor of the electronic nose undergoes one or more temperature oscillations resulting in sensor-voltage-output waveforms generated over the course of the sensor temperature changes. In this embodiment, the sensing apparatus enables alterations to the temperature of each sensor according to a defined temperature waveform using thermistors to alter the sensor temperatures.

For each labeled VOC sample of the training sample set, the method conducts multiple sensing sessions, resulting in a set of voltage outputs from the sensor array for each labeled VOC sample. The values for each feature of each labeled VOC may vary across the set of voltage outputs for the VOC. The set of voltage outputs defines a distribution of values associated with each feature of the set of features for the VOC.

For each labeled VOC of the training data set, the method learns a class, a set of m features, corresponding to that VOC. For each feature of each class, the method learns and defines the feature boundaries by analyzing the distribution of feature values from the set of outputs associated with the sensing sessions for the labeled VOC.

In an embodiment, to reduce computational complexity, the method reduces the set of m features associated with each labeled VOC. In this embodiment, for the distribution of values for each feature of each class, the method tests each value for inclusion in the set of values for the feature and the class. For each class, the method considers an m-dimensional real vector, where m equals the overall set of features associated with a VOC sample. Evaluation of the set of features includes defining boundaries for each feature of the set of features.

The method defines the boundaries for each feature of the class by estimating the mean ($\mu_j$), and standard deviation ($\sigma_j$) for the distribution of feature values using a distribution including surrogate data for a specified level of confidence, e.g., 95% confidence. The boundaries of the feature are then determined according to Chebyshev's inequality and a first threshold value defined as $\mu_j \pm n_j^* \sigma_j$. The method obtains a value of each hyperparameter $n_j$ as the smallest number which allows Z % of the values of the distribution to be included in the interval defined as $[\mu_j - n_j^* \sigma_j, \mu_j + n_j^* \sigma_j]$, using user input to define the Z %, e.g., 95%. As a result of this consideration, the method yields a set of feature boundaries $\mu_0 \pm n_0^* \sigma_0, \mu_1 \pm n_1^* \sigma_1, \ldots, \mu_{m^*} \pm n_{m^*}^* \sigma_{m^*}$ wherein m*<m. For the defined boundaries of the example, 95% of the feature data falls within the boundaries and 5% of the feature data falls outside the defined boundaries. The method excludes features having dispersed distributions indicated by hyperparameter $n_j$ values above a threshold from the class, resulting in 95%, or other user defined limits, of the set of training sample data features being associated with a labeled VOC and 5% of the training sample data features being anomalous to the labeled VOC.

The method populates a VOC database with the feature boundaries defined and associated with each of the labeled VOCs and VOC sets included in the training samples. The method compares test sample data to the feature boundary sets of the VOC database to classify test samples according to VOC content.

After training, the method provides the classification model for use with array sensor output voltages associated with test samples—those sample which are not part of the training samples set. For each test sample, the method divides the output voltage data into features having the same temporal scale as that used in segmenting the training sample data. For each feature of each sensor output for each test sample, the method compares the feature to the boundaries of corresponding features from the respective VOCs of the model. The method considers features to be corresponding when the two features occupy the same position along the voltage output timeline.

In an embodiment, the method classifies test samples having values falling outside the defined feature boundaries of more than a defined maximum number of features (Max), as an anomaly. In this embodiment, the method defines the maximum number according to the distribution of training sample data for the features. For the training set data, the method begins with Max=0, representing circumstances wherein all samples are classified as anomalies, and increases Max linearly in steps of 1, until the number of anomalies in the training sample set for classified as anomalies is less than or equal to the complement of the user defined confidence level, (100−Z) % of the training samples. For example, the method defines Max as the number of features having boundaries exceeded by the training sample data when 5% of the training samples are classified as anomalies for a user-defined Z of 95. In practice, the method classifies test samples as anomalies when the number of test sample feature values outside the defined feature boundaries $\mu_0 \pm n_0^* \sigma_0, \mu_1 \pm n_1^* \sigma_1, \ldots, \mu_{m^*} \pm n_{m^*}^* \sigma_{m^*}$, exceeds the value of Max determined according to the training sample data set. Test samples having fewer than Max feature values falling outside the defined feature boundaries are classified as the VOC having the greatest number of matched features relative to the test sample data feature values.

In an embodiment, the method defines a value a, as the number of test sample feature values falling outside the corresponding feature boundaries. For test samples having a≥Max, the method classifies the test sample as an anomaly. Higher values of a indicate a higher degree of anomaly for the test sample relative to the baseline VOCs of the trained model. For test samples classified as anomalous, the method considers the degree of anomaly, and classifies the test samples as either members of an unseen class (relatively low degrees of anomaly) not currently represented in the VOC database of the model, or as contaminated samples (relatively high degrees of anomaly).

In an embodiment, the method defines a threshold for a as the average value of a for the training samples falling outside the feature boundaries as the method defines those boundaries. (For a Z of 95, the method defines feature boundaries to include 95% of the training samples, the method then uses the average a value of the 5% of the training samples falling outside the now defined feature boundaries as the threshold for further classifying anomalous test samples as either unseen class samples, if a is below the threshold, or contaminated samples, if a is above the threshold.

In an embodiment, the method labels test samples having a values at or above the "a" threshold as contaminants, and assigns the samples to a contaminant class. Unsupervised application of the method to the contaminant class samples yields new classes of VOCs associated with specific types of contamination according to the test sample feature values, having similar features. In this embodiment, the method utilizes the feature sets of the test samples classified as contaminated and further categorizes the overall set of classified samples according to similarities in the respective feature sets of the samples. The new categorizations for contaminants may be added to the database of baseline VOCs for use in classifying new test samples.

For test samples classified as anomalous but having a values falling below the "a" threshold, the method classifies the test sample to an unseen class. Unsupervised application of the method to the test samples classified as unseen further categorizes the test samples according to similarities between the feature sets of the samples. The new categorizations may be added to the database of baseline VOCs for use in classifying new test samples.

In an embodiment, the sensors of the array may be subject to a shift in output due to degradation of the sensor with use. In this embodiment, the thresholds described above may shift in response to shifts in the sensor outputs. Performing the method in a training mode may result in the determination of new threshold values corresponding to sensor changes. In this embodiment, operation of the method in training mode to check and revise thresholds may be conducted on periodic bases, monthly, semi-annually, annually, etc.

Applications of the disclosed embodiments include testing food samples to check for spoliation as indicated by a shift in sample VOCs from a defined baseline, for meat, dairy and other food products. Further applications include checking for the presence of volatile organic compounds associated with hazardous materials, e.g., the VOC added to commercially available natural gas to assist in identifying system leaks, checking for the presence of ammonia gas near refrigeration systems using that gas, checking for baseline volatile organic compounds emanating from other hazardous materials such as explosive materials, etc. Uses further include sensing VOCs associated with disease as a diagnostic indicator.

Figure 1:
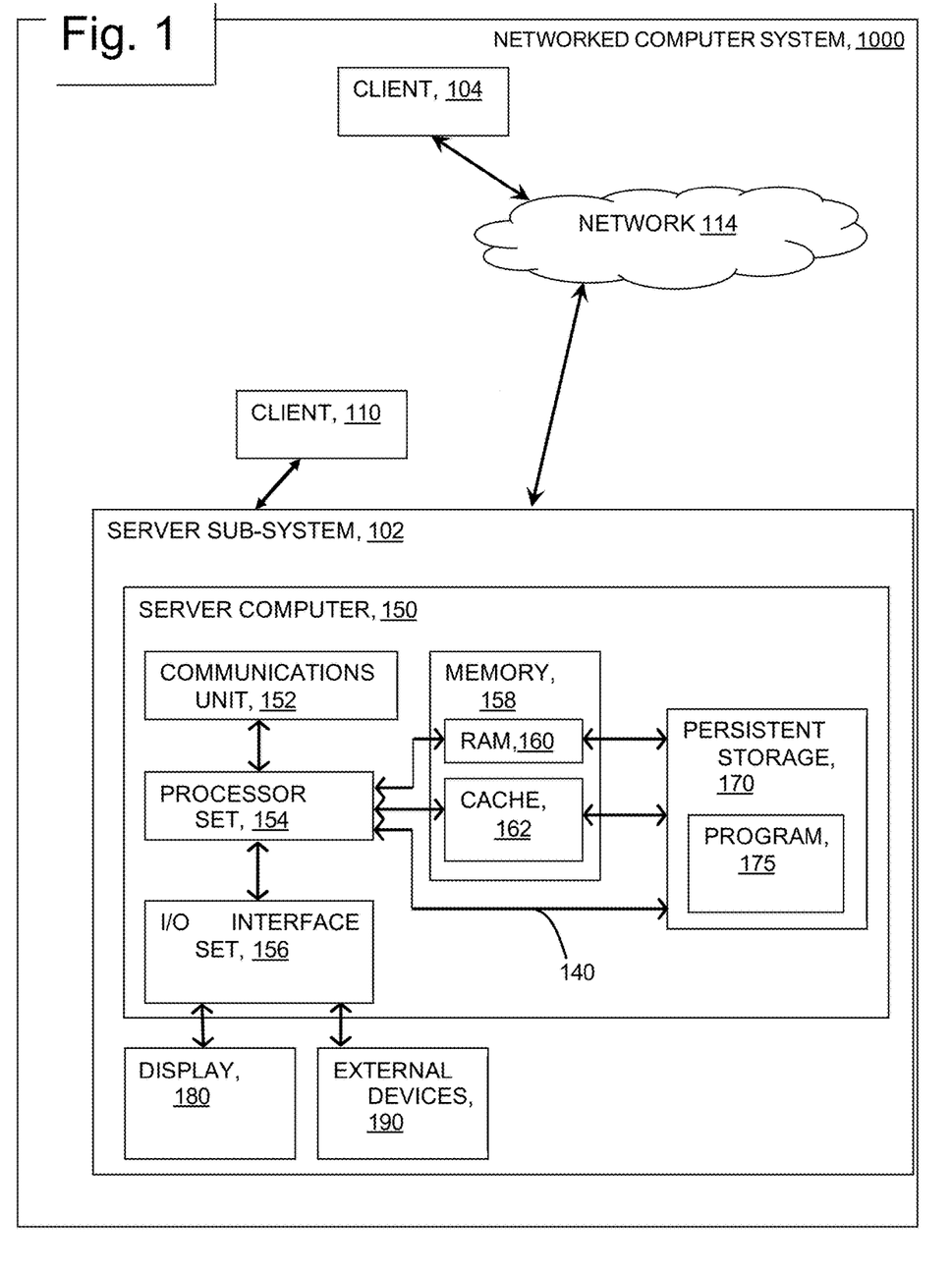
FIG. 1 provides a schematic illustration of a computing environment, according to an embodiment of the invention.

FIG. 1 provides a schematic illustration of exemplary network resources associated with practicing the disclosed inventions. The inventions may be practiced in the processors of any of the disclosed elements which process an instruction stream. As shown in the figure, a networked Client device 110 connects wirelessly to server sub-system 102. Client device 104 connects wirelessly to server sub-system 102 via network 114. Client devices 104 and 110 comprise volatile organic compound classification program (not shown) together with sufficient computing resource (processor, memory, network communications hardware) to execute the program. As shown in FIG. 1, server sub-system 102 comprises a server computer 150. FIG. 1 depicts a block diagram of components of server computer 150 within a networked computer system 1000, in accordance with an embodiment of the present invention. It should be appreciated that FIG. 1 provides only an illustration of one implementation and does not imply any limitations with regard to the environments in which different embodiments can be implemented. Many modifications to the depicted environment can be made.

Server computer 150 can include processor(s) 154, memory 158, persistent storage 170, communications unit 152, input/output (I/O) interface(s) 156 and communications fabric 140. Communications fabric 140 provides communications between cache 162, memory 158, persistent storage 170, communications unit 152, and input/output (I/O) interface(s) 156. Communications fabric 140 can be implemented with any architecture designed for passing data and/or control information between processors (such as microprocessors, communications and network processors, etc.), system memory, peripheral devices, and any other hardware components within a system. For example, communications fabric 140 can be implemented with one or more buses.

Memory 158 and persistent storage 170 are computer readable storage media. In this embodiment, memory 158 includes random-access memory (RAM) 160. In general, memory 158 can include any suitable volatile or non-volatile computer-readable storage media. Cache 162 is a fast memory that enhances the performance of processor(s) 154 by holding recently-accessed data, and data near recently-accessed data, from memory 158.

Program instructions and data used to practice embodiments of the present invention, e.g., the volatile organic compound classification program 175, are stored in persistent storage 170 for execution and/or access by one or more of the respective processor(s) 154 of server computer 150 via cache 162. In this embodiment, persistent storage 170 includes a magnetic hard disk drive. Alternatively, or in addition to a magnetic hard disk drive, persistent storage 170 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 170 may also be removable. For example, a removable hard drive may be used for persistent storage 170. Other examples include optical and magnetic disks, thumb drives, and smart cards that are inserted into a drive for transfer onto another computer readable storage medium that is also part of persistent storage 170.

Communications unit 152, in these examples, provides for communications with other data-processing systems or devices, including resources of client computing devices 104, and 110. In these examples, communications unit 152 includes one or more network interface cards. Communications unit 152 may provide communications through the use of either or both physical and wireless communications links. Software distribution programs, and other programs and data used for implementation of the present invention, may be downloaded to persistent storage 170 of server computer 150 through communications unit 152.

I/O interface(s) 156 allows for input and output of data with other devices that may be connected to server computer 150. For example, I/O interface(s) 156 may provide a connection to external device(s) 190 such as a keyboard, a keypad, a touch screen, a microphone, a digital camera, and/or some other suitable input device. External device(s) 190 can also include portable computer readable storage media such as, for example, thumb drives, portable optical or magnetic disks, and memory cards. Software and data used to practice embodiments of the present invention, e.g., volatile organic compound classification program 175 on server computer 150, can be stored on such portable computer readable storage media and can be loaded onto persistent storage 170 via I/O interface(s) 156. I/O interface(s) 156 also connect to a display 180.

Display 180 provides a mechanism to display data to a user and may be, for example, a computer monitor. Display 180 can also function as a touch screen, such as a display of a tablet computer.

Figure 2:
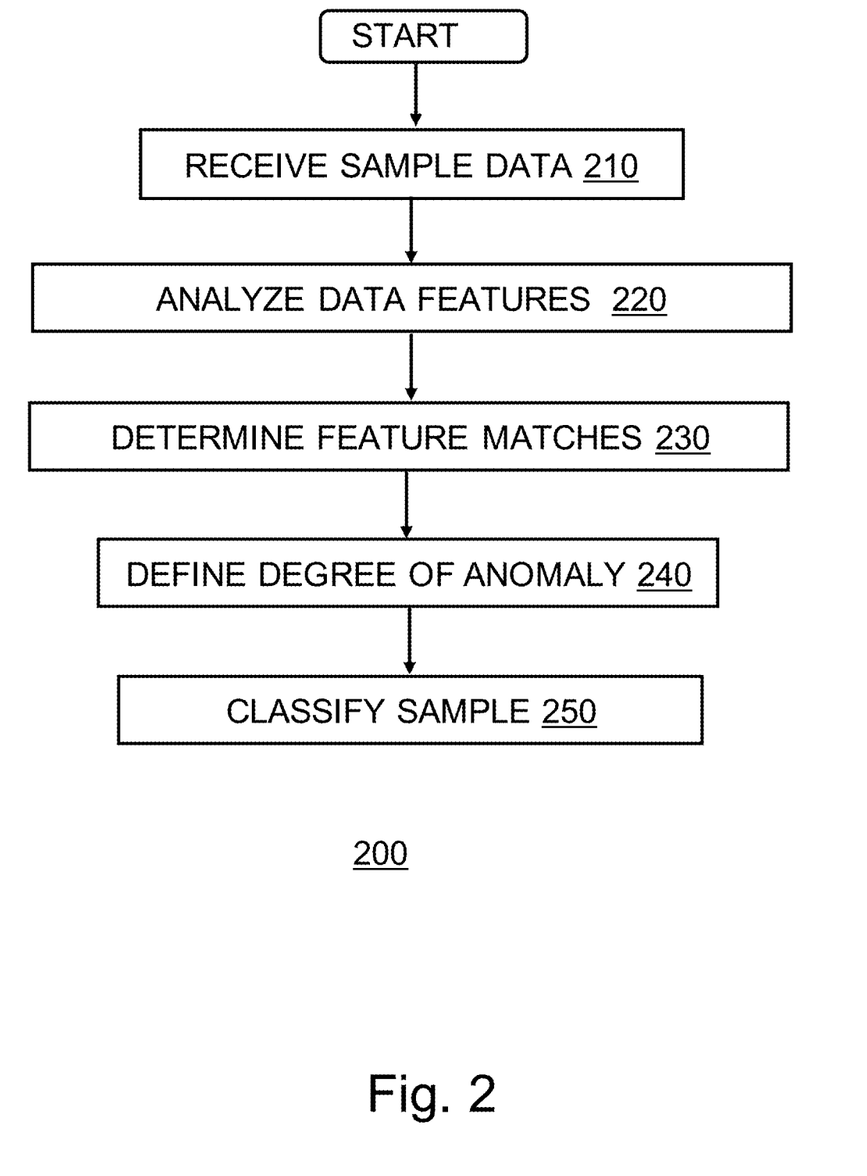
FIG. 2 provides a flowchart depicting an operational sequence, according to an embodiment of the invention.

FIG. 2 provides a flowchart 200, illustrating exemplary activities associated with the practice of the disclosure. After program start, at block 210, the method of volatile organic compound classification program 175 receives sensor array output voltage data associated with VOCs, from an electronic nose, as test data. The method may receive the data through a direct connection to an electronic nose or indirectly after such data has been recorded for processing and passed to the method. Either direct or indirect connections may include passing data to the method over a computer network infrastructure. The method translates the received VOC data into data features for use in classifying the test sample according to the VOC content of the sample.

At block 220, the method of volatile organic compound classification program 175 analyses the test data according to a set of baseline VOC feature patterns stored in a database. In an embodiment, the method has populated the VOC database by analyzing labeled VOC sample data according to the classification steps of the method. The method defines feature boundaries for the training sample data features. The method defines thresholds used for classifying test samples as anomalous, and further characterizes anomalous test samples as either contaminated samples or unseen VOC samples.

At block 230, the method determines matches between test sample data features and data feature patterns for classified VOCs. The method compares test sample data feature values with previously defined data feature boundaries for corresponding VOC data features. Values within the defined boundaries are considered a match, and those outside the defined boundaries are not considered a match. The method determines the number of test sample data features which match known VOC data features and how many test sample data features do not match known VOC data features.

At block 240, the method defines a first degree of anomaly for the test sample data. The method uses the number of matches determined above to define the first degree of anomaly. The method determines a number, a, representing the number of test sample data features that fell outside defined training sample VOC data feature boundaries. The method carries the a values forward as the first degree of anomaly of the test sample.

At block 250, the method classifies the test sample according to the first degree of anomaly. In an embodiment, the method defines a Max threshold value for test sample data features' a values, according to the distribution of data from the training samples. The method determines the threshold number of data feature boundaries, which yields a user-specified level of accuracy in classifying training data samples. As an example, the method determines the maximum number of unmatched training sample data feature boundaries, which results in an anomalous classification for a number of training samples, which is less than or equal to a user-defined tolerance level. For a user-defined confidence of 95%, 5% anomaly tolerance, the method determines the maximum number of feature boundaries that training set samples may fall outside, which results in 5% or less of the training samples being classified as anomalous.

Test samples having a values below the threshold are classified as the baseline VOC having the largest number of feature matches with the test sample data features. Test samples having a values above the defined a threshold are classified as anomalies.

Figure 3:
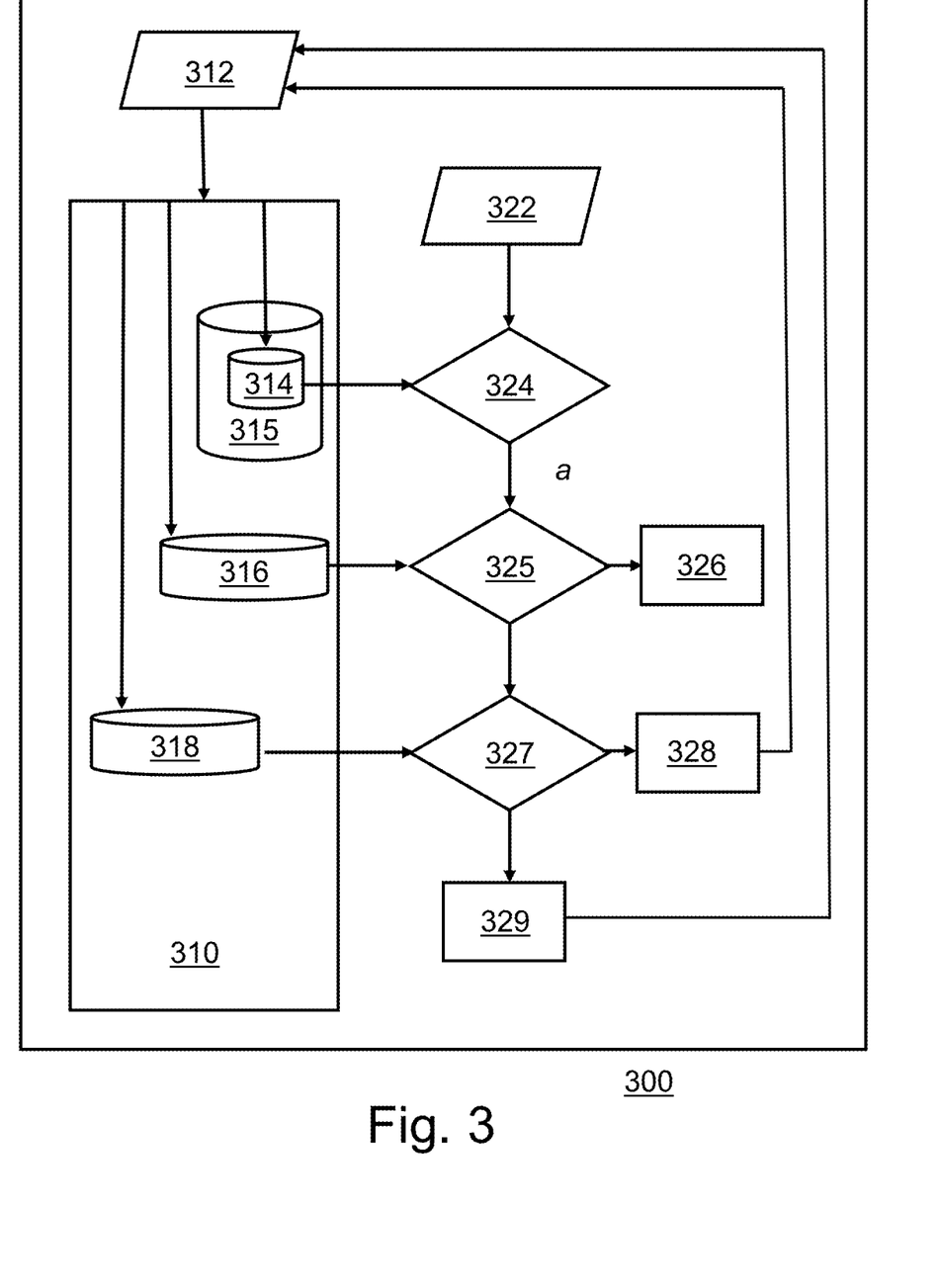
FIG. 3 provides a flowchart depicting logical data flow, according to an embodiment of the invention.

FIG. 3 provides a flowchart 300 illustrating method logic and data flow associated with training a model, according to an embodiment of the invention. As shown in the Figure, a machine-learning classification model 310, receives training sample sensor array output data 312. The model 310 uses the data 312 to define data features boundaries 314 according to a user confidence level Z, for labeled VOCs. The method stores the patterns of feature boundaries for the labeled VOCs in a VOC feature boundary database 315. The model further defines a MAX threshold 316, associated with the number of feature boundaries sample data may fall outside without being classified as anomalous. The method determines the MAX threshold 316, according to the user confidence and the distribution of sample data features from the training sample set. The method also determines an "a" threshold 318 for anomaly classification. The method determines the "a" threshold 318 as the average value of a, the number of failed feature boundary matches, for the samples of the training set which were classified as anomalous. For an anomaly tolerance level of 5%, the method determines the "a" threshold 318 as the average "a" value for the 5% of the training set samples classified as anomalous.

As shown in the figure, the method utilizes the trained model 310, including the feature boundary definitions 314, the MAX threshold 316, and the "a" threshold 318, to classify new test sample data 322. The trained model receives test sample data 322, and compares the test sample data features with stored VOC data features boundaries 314 from the model's VOC feature boundary database 315, at 324. For each test sample, the method determines the number of VOC feature boundaries the sample's data features match and how many the sample's features do not match—the "a" value for the test sample.

At 325, the method compares the test sample's "a" value to the previously determined MAX threshold 316 value. For test samples having an "a" value less than MAX, the method classifies the test sample as the VOC having the most data feature matches with the sample 326. For test samples having a values≥MAX, the method classifies the test sample as an anomaly 327.

For test samples classified as anomalies, at 327 the method compares the sample's a value with the "a" threshold 318. Test samples having an "a" value above the "a" threshold 318 are classified as contaminants 328. Test samples having a values less than the "a" threshold are classified as unseen volatile organic compounds 329.

In an embodiment where sufficient contaminant samples, or unseen volatile organic compound samples have accumulated, the method conducts a training phase using the accumulated contaminant or unseen volatile organic compound data as new training data 312 to generate new classifications for the model.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
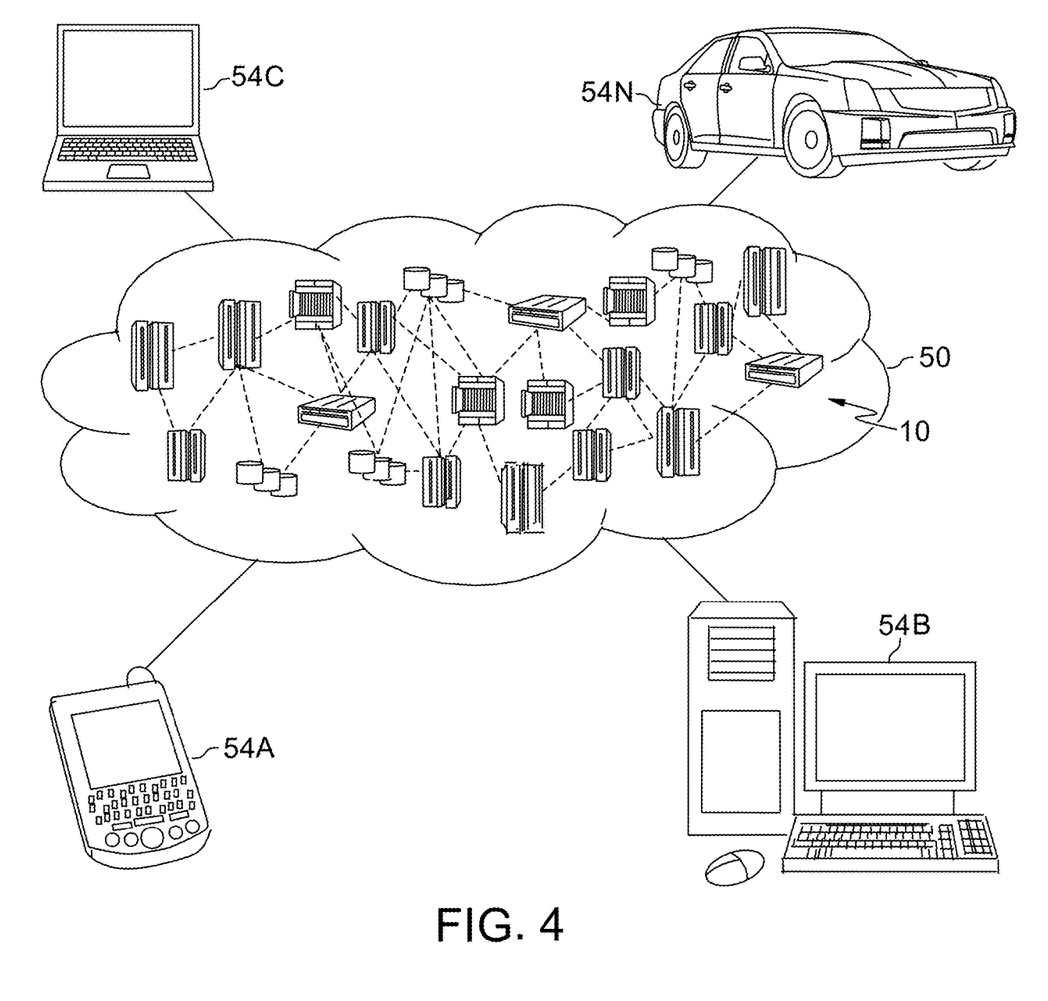
FIG. 4 depicts a cloud-computing environment, according to an embodiment of the invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
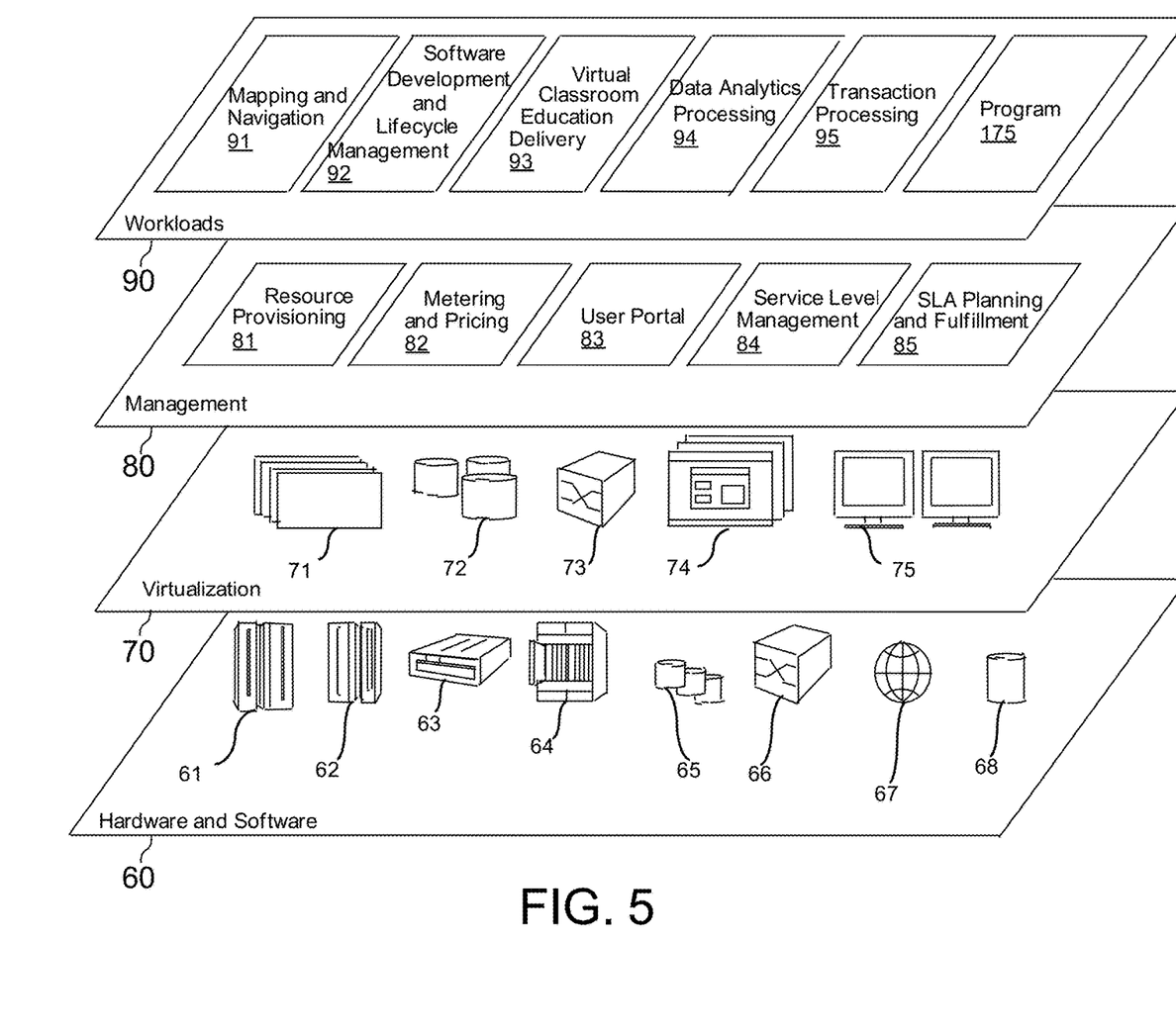
FIG. 5 depicts abstraction model layers, according to an embodiment of the invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and volatile organic compound classification program 175.

The present invention may be a system, a method, and/or a computer program product at any possible technical detail level of integration. The invention may be beneficially practiced in any system, single or parallel, which processes an instruction stream. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, or computer readable storage device, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions collectively stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer implemented method for volatile organic compound classification, the method comprising:
    subjecting, by one or more computer processors, a set of sensors of an electronic nose to a temperature oscillation;
    gathering, by the one or more computer processors, electronic nose voltage outputs for a set of known volatile organic compounds (VOCs) as the set of sensors of the electronic nose undergo the temperature oscillation;
    learning, by the one or more computer processors, a set of data features corresponding to each of the known VOCs according to the voltage outputs;
    receiving, by the one or more computer processors, test data associated with detecting VOCs;
    analyzing, by the one or more computer processors, the test data according to the set of data features associated with the known VOCs;
    determining, by the one or more computer processors, a match between each feature of the test data and a corresponding feature of the set of data features, yielding a set of matches, wherein determining a match between each feature of the test data and the corresponding feature of the set of data features comprises determining a match according to a second degree of anomaly;
    defining, by the one or more computer processors, a first degree of anomaly for the test data according to the set of matches; and
    classifying, by the one or more computer processors, the test data according to the first degree of anomaly.

2. The computer implemented method according to claim 1, wherein the second degree of anomaly is determined according to a first threshold associated with a distribution of the corresponding feature in a set of training samples.

3. The computer implemented method according to claim 1, further comprising:
    classifying, by the one or more computer processors, the test data as anomalous, according to the first degree of anomaly.

4. The computer implemented method according to claim 3, further comprising classifying, by the one or more computer processors, the test data as an unseen class according to a third degree of anomaly.

5. The computer implemented method according to claim 3, further comprising classifying, by the one or more computer processors, the test data as contaminated according to a third degree of anomaly.

6. The computer implemented method according to claim 5, wherein the third degree of anomaly is associated with a distribution of anomalous data samples in a set of training samples.

7. A computer program product for volatile organic compounds classification, the computer program product comprising one or more computer readable storage devices and collectively stored program instructions on the one or more computer readable storage devices, the stored program instructions comprising:
    program instructions to subject a set of sensors of an electronic nose to a temperature oscillation;
    program instructions to gather electronic nose voltage outputs for a set of a known volatile organic compounds (VOCs) as the set of sensors of the electronic nose undergo the temperature oscillation;
    program instructions to learn a set of data features corresponding to each of the known VOCs;
    program instructions to receive test data associated with detecting VOCs;
    program instructions to analyze the test data according to the set of data features associated with the known VOCs;
    program instructions to determine a match between each feature of the test data and a corresponding feature of the set of data features, yielding a set of matches, wherein determining a match between each feature of the test data and the corresponding feature of a set of data features comprises determining a match according to a second degree of anomaly;
    program instructions to define a first degree of anomaly for the test data according to the set of matches; and
    program instructions to classify the test data according to the first degree of anomaly.

8. The computer program product according to claim 7, wherein the second degree of anomaly is determined according to a first threshold associated with a distribution of the corresponding feature in a set of training samples.

9. The computer program product according to claim 7, the stored program instructions further comprising:
    program instructions to classify the test data as anomalous, according to the first degree of anomaly.

10. The computer program product according to claim 9, the stored program instructions further comprising program instructions to classify the test data as an unseen class according to a third degree of anomaly.

11. The computer program product according to claim 9, the stored program instructions further comprising program instructions to classify the test data as contaminated according to a third degree of anomaly.

12. The computer program product according to claim 11, wherein the third degree of anomaly is associated with a distribution of anomalous data samples in a set of training samples.

13. A computer-implemented method for volatile organic compounds classification according to an array of sensors whose voltage output is a function of volatile organic compounds (VOCs) present in a given test sample that is in contact with the array, the method comprising:
- subjecting, by one or more processors, a set of sensors of an electronic nose to a temperature oscillation;
- gathering, by one or more computer processors, sensor voltage outputs for a set of known volatile organic compounds (VOCs) as the sensors undergo the temperature oscillation;
- learning, by the one or more computer processors, a set of data features corresponding to each of the known VOCs according to the voltage outputs;
- populating a database according to the sets of features;
- receiving a sample voltage output from the array, the voltage output associated with a test sample;
- analyzing, by one or more computer processors, the sample voltage output to match the features that correspond to various organic compounds;
- for each feature associated with each VOC of a database of known VOCs, determining whether the test sample voltage output matches the feature according to a first threshold for the feature;
- determining a first degree of anomaly for the test sample, the first degree of anomaly comprising the number of unmatched features; and
- classifying the test sample according to the sample voltage output matches.

14. The computer-implemented method according to claim 13, wherein the first threshold is determined according to a distribution of the feature in a set of VOC training samples.

15. The computer-implemented method according to claim 13, further comprising:
- applying a second threshold to the first degree of anomaly, the second threshold computed in view of a second degree of anomaly computed in a subset of VOC training samples corresponding to anomalous samples; and
- classifying test samples associated with first degrees of anomaly exceeding the second threshold, as anomalous test samples.

16. The computer-implemented method according to claim 15, further comprising:
- applying a third threshold to the first degree of anomaly of the anomalous test samples, the third threshold computed in view of a second degree of anomaly computed in a subset of VOC training samples corresponding to anomalous samples; and
- classifying test samples below the third threshold as unseen VOC samples.

17. The computer-implemented method according to claim 15, further comprising:
- analyzing the anomalous test samples; and
- updating the database of known VOCs according to the analysis.

* * * * *